United States Patent [19]

Schade et al.

[11] Patent Number: 4,686,236

[45] Date of Patent: Aug. 11, 1987

[54] 3-(3-IODOPROPARGYLOXY)-PROPIONI-TRILE, A PROCESS FOR ITS PREPARATION AND ITS USE

[75] Inventors: Gerold Schade, Cologne; Wilfried Paulus; Hans-Georg Schmitt, both of Krefeld, all of Fed. Rep. of Germany

[73] Assignee: Bayer Aktiengesellschaft, Leverkusen, Fed. Rep. of Germany

[21] Appl. No.: 881,557

[22] Filed: Jul. 3, 1986

[30] Foreign Application Priority Data

Jul. 26, 1985 [DE] Fed. Rep. of Germany ....... 3526789

[51] Int. Cl.⁴ ...................... A01N 37/34; C01C 121/30
[52] U.S. Cl. .................................. 514/526; 558/449
[58] Field of Search ........................ 558/449; 514/526

[56] References Cited

U.S. PATENT DOCUMENTS

| 2,280,790 | 4/1942 | Bruson ................................. 558/449 |
| 2,403,686 | 7/1946 | Schwoegler ...................... 558/449 X |
| 2,809,988 | 10/1957 | Heininger ........................... 558/449 |
| 4,115,326 | 9/1978 | Plattier et al. .................. 558/449 X |
| 4,322,442 | 3/1982 | Jäger et al. ...................... 514/526 X |

FOREIGN PATENT DOCUMENTS 3304899  8/1984  Fed. Rep. of Germany .
84/00159  1/1984  PCT Int'l Appl. .

OTHER PUBLICATIONS

Weygand/Hilgetag, "Preparative Organic Chemistry", (1972), pp. 159–161, John Wiley & Sons, New York, London, Sydney, Toronto.

C. A.; 68:49008b, Shostakovskii et al (1968).

Primary Examiner—Joseph Paul Brust
Attorney, Agent, or Firm—Sprung, Horn, Kramer & Woods

[57] ABSTRACT 3-(3-iodopropargyloxy)-propionitrile of the formula

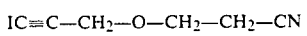

is prepared by iodination of propargyloxypropionitrile. The 3-(3-iodopropargyloxy)-propionitrile is used as an active compound in microbicidal agents.

8 Claims, No Drawings

3-(3-IODOPROPARGYLOXY)-PROPIONITRILE, A PROCESS FOR ITS PREPARATION AND ITS USE

BACKGROUND OF THE INVENTION

The invention relates to the new compound 3-(3-iodopropargyloxy)-propionitrile, a process for its preparation and its use in microbicidal agents.

Di- and triethylene glycol alkyl/aryl 3-iodo-2-propinyl ethers and substituted 1-(3-iodo-2-propinyloxy-)-2- and -3-propanols which are used as antimicrobial agents are known from DE-OS (German Published Specification) No. 3,224,503 and DE-OS (German Published Specification) No. 3,304,899.

Although the compounds described in the German Offenlegungsschriften (German Published Specifications) in general have a high microbicidal activity, their production and use in preservatives is severely impaired by their physical properties. In particular, the compounds are in general not crystalline, but are oils. Purification of the compounds is thereby made difficult. Purification is, however, in all cases essential to remove discolorations and impurities caused by the production, since colored active compounds cannot be used for the preservation of colourless products. Moreover, from the toxicological viewpoint, it is desirable for the compounds employed to be free from impurities.

Purification by distillation, which is otherwise customary for liquids, cannot be carried out on an industrial scale on the iodopropargyl compounds such as are described in the German Offenlegungsschriften (German Published Specifications) mentioned, because these compounds are unstable to heat and can thereby decompose even explosively (compare H. G. Viehe, *Chemistry of Acetylenes*, New York 1969, page 691).

SUMMARY OF THE INVENTION

Surprisingly, it has now been found that the new compound iodopropargyloxypropionitrile of the formula I

IC≡C—CH₂—O—CH₂—CH₂—CN    I not only has a powerful microbicidal activity, but also has physical properties which do not give rise to the above-mentioned problems. The new compound iodopropargyloxypropionitrile is a crystalline solid of high melting point (66°-68° C.). No melting occurs during production. In addition, the new compound has such a high tendency towards crystallization that it is obtained in the crystalline form and in a high purity immediately on preparation. If necessary, the new compound can be prepared in a virtually entirely pure form by simple recrystallization.

The new compound iodopropargyloxypropionitrile of the formula I is prepared by iodination of propargyloxypropionitrile of the formula II

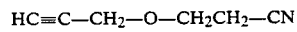

HC≡C—CH₂—O—CH₂CH₂—CN    II with iodinating agents in the presence of solvents and/or diluents and in the presence of bases at temperatures from −10° C. to +30° C.

DETAILED DESCRIPTION OF THE INVENTION

Iodinating agents which can be employed in the process according to the invention are iodine and/or compounds which supply iodide ions, such as sodium iodide and ammonium iodide, in the presence of oxidizing agents, such as sodium hypochlorite, calcium hypochlorite and hydrogen peroxide.

Suitable bases are both inorganic and organic bases, such as sodium hydroxide, calcium hydroxide, sodium methylate, potassium tert.-butylate and sodium isobutylate, preferably sodium hydroxide and sodium methylate.

Suitable solvents for the process according to the invention are, for example, water alcohols, such as methanol and/or ethanol, or mixtures thereof. The iodination is preferably carried out at temperatures from −5° C. to +20° C.

According to the invention, 1 mole of propargyloxypropionitrile of the formula II is treated with about 1.0 to 1.5 moles of iodinating agent, preferably 1.0 to 1.2 moles of iodinating agent.

The particular most favorable amounts of bases and solvents and/or diluents can easily be determined by preliminary experiments. About 1 to 3, preferably 1.2 to 2, moles of base per mole of propargyloxypropionitrile of the general formula II and the same to five times, preferably twice to three times, the amount by weight of solvent and/or diluent are usually employed.

Propargyloxypropionitrile of the formula II is a known compound (see *Chem. Abstr.*, 68, 49008). This compound is prepared by addition of propargyl alcohol onto acrylonitrile in the presence of basic catalysts.

Because of its powerful microbicidal activity and its broad action spectrum, the new compound 3-(3-iodopropargyloxy)-propionitrile can advantageously be used for combating microorganisms, in particular for the preservation of industrial materials. As the comparison examples show, it is considerably more effective than, for example, the iodopropargyl ether 1-(3-iodo-2-propinyloxy)-propane-2,3-diol known from DE-OS (German Published Specification) No. 3,304,899.

According to the invention, industrial materials are non-living materials which have been prepared for use in industry. Examples of industrial materials which are to be protected by the active compound according to the invention from microbial change or destruction can be adhesives, sizes, paper and card, textiles, leather, wood, paints and articles made of plastic, cooling lubricants and other materials which can be attacked or destroyed by microorganisms. Components of production plants, for example cooling water circulations, which can be impaired by multiplication of microorganisms, may also be mentioned in the context of the materials to be preserved. Industrial materials which may be mentioned as preferred in the context of the present invention are adhesives, sizes, paper and card, leather, wood, paints, cooling lubricants and cooling circulations, particularly preferably wood.

Examples which may be mentioned of microorganisms which can effect degradation of or a change in the industrial materials are bacteria, fungi, yeasts, algae and slime organisms. The active compound according to the invention preferentially acts against fungi, in particular moulds and fungi which discolor and destroy wood (Basidiomycetes), and against slime organisms and algae.

Microorganisms of the following genera may be mentioned as examples: Alternaria, such as *Alternaria tenuis*, Aspergillus, such as *Aspergillus niger*, Chaetomium, such as *Chaetomium globosum*, Coniophora, such as *Coniophora puteana*, Lentinus, such as *Lentinus tigrinus*, Penicillium, such as *Penicillium glaucum,* Polyporus, such as *Polyporus versicolor,* Aureobasidium, such as *Aureobasidium pullulans,* Sclerophoma, such as *Sclerophoma pityophila,* Trichoderma, such as *Trichoderma viride,* Escherichia, such as *Escherichia coli,* Pseudomonas, such as *Pseudomonas aeruginosa* and Staphylococcus, such as *Staphylococcus aureus.*

The active compound according to the invention can be converted into the customary formulations, such as solutions, emulsions, suspensions, powders, pastes and granules, depending on the field of use.

These can be prepared in a manner which is known per se, for example by mixing the active compound with an extender, which consists of a liquid solvent and/or solid excipients, if appropriate using surface-active agents, such as emulsifiers and/or dispersing agents, and, in the case of the use of water as an extender, organic solvents, such as alcohols, may be used, if appropriate, as auxiliaries.

Liquid solvents for the active compound can be, for example, water, alcohols, such as lower aliphatic alcohols, preferably ethanol or isopropanol, or benzyl alcohol, ketones, such as acetone or methyl ethyl ketone, liquid hydrocarbons, such as benzine fractions, and halogenated hydrocarbons, such as 1,2-dichloroethane.

Microbicidal agents in general contain the active compound in an amount of 1 to 95%, preferably 10 to 75%.

The use concentration of the active compound according to the invention depends on the nature and occurrence of the microorganisms to be combated and on the composition of the material to be preserved. The optimum amount to be used can be determined by test series. The use concentrations are in general in the range from 0.001 to 5% by weight, preferably 0.05 to 1.0% by weight, based on the material to be preserved.

The active compound according to the invention can also be present in a mixture with other known active compounds. The following active compounds may be mentioned as examples: benzyl alcohol mono(poly)-hemiformal and other compounds which split off formaldehyde, benzimidazolyl methylcarbamates, tetramethylthiuram disulphide, zinc salts of dialkyldithiocarbamates, 2,4,5,6-tetrachloroisophthalonitrile, thiazolylbenzimidazole, mercaptobenzothiazole, 2-thiocyanatomethylthio-benzothiazole, organo-tin compounds, methylene bisthiocyanate, phenol derivatives, such as 2-phenylphenol, (2,2'-dihydroxy-5,5'-dichloro)-diphenylmethane and 3-methyl-4-chloro-phenol.

PREPARATION EXAMPLE

Example 1

230 g (0.9 mole) of iodine are added in portions to 86.3 g (0.8 mole) of propargyloxypropionitrile, 71 g of 50% strength NaOH and 500 ml of methanol at 0° to 5° C. The mixture is subsequently stirred for 1 hour, decolorized with NaHSO$_3$ solution, poured into 1.5 l of ice-water and filtered with suction. Yield: 154 g (83%) of pale yellowish crystals, melting point 65° to 68° C., purity 98.5% (gas chromatography).

After recrystallization from cyclohexane, colourless crystals, melting point 66° to 68° C., purity 100% (gas chromatography).

USE EXAMPLES

Example 2

To demonstrate the activity against fungi, the minimum inhibitory concentrations (MIC) of active compounds according to the invention are determined:

Active compounds according to the invention are added in concentrations of 0.1 mg/l to 500 mg/l to an agar prepared from beer wort and peptone. After the agar has solidified, it is contaminated with pure cultures of the test organisms listed in the table. After storage at 28° C. and 60 to 70% relative atmospheric humidity for 2 weeks, the MIC is determined. The MIC is the lowest concentration of active compound at which the species of microbe used does not grow at all, and is given in the following table.

TABLE

MICs in mg/l on action of the substances according to the inventions on fungi

| Test organisms | Substance according to the invention | Comparison substance* |
|---|---|---|
| *Alternaria tenuis* | 5 | 50 |
| *Aspergillus niger* | 5 | 50 |
| *Aureobasidium pullulans* | 5 | 50 |
| *Chaetomium globosum* | 20 | 100 |
| *Cladeosporium cladesporioides* | 5 | |
| *Lentinus tigrinus* | 15 | 50 |
| *Penicillium glaucum* | 5 | 50 |
| *Sclerophoma pityophila* | 5 | 50 |
| *Trichoderma viride* | 20 | 500 |

*1-(3-iodo-2-propinyloxy)-propane-2,3-diol/compound of Example 73 of DE-OS (German Published Specification) 3,304,899.

Example 3

(Action against slime organisms)

The substance according to the invention is used in concentrations of in each case 0.1 to 100 mg/l in Allens nutrient solution (*Arch. Mikrobiol.,* 17, 34 to 53 (1952)), which contains, in 4 l of sterile water, 0.2 g of ammonium chloride, 4.0 g of sodium nitrate, 1.0 g of dipotassium hydrogen phosphate, 0.2 g of calcium chloride, 2.05 g of magnesium sulphate, 0.02 g of iron chloride and 1% of caprolactam, dissolved in a little acetone. Shortly beforehand, the nutrient solution is infected with slime organisms (about $10^6$ germs/ml) which have been isolated from spinning water circulations used in polyamide production. Nutrient solutions which contain the minimum inhibitory concentration (MIC) or higher concentrations of active compound are still completely clear after culture for 3 weeks at room temperature, that is to say the intense multiplication of the microbes and slime formation noticeable after 3 to 4 days in nutrient solutions containing no active compound are absent.

Table II

MIC values in mg/l on action of the substances shown below on slime organisms

| Active compound | MIC in mg/l |
|---|---|
| According to the invention | 15 |
| Comparison substance = 1-(3-Iodo-2-propinyloxy)-propane-2,3-diol | 35 |

It will be appreciated that the instant specification and claims are set forth by way of illustration and not limitation, and that various modifications and changes may be made without departing from the spirit and scope of the present invention.

We claim:

1. 3-(3-iodopropargyloxy)propionitrile of the formula

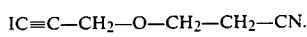
$$IC{\equiv}C-CH_2-O-CH_2-CH_2-CN.$$

2. A microbicidal agent comprising as an active agent a microbicidally effective amount of a 3-(3-iodopropargyloxy)-propionitrile of the formula

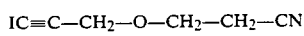
$$IC{\equiv}C-CH_2-O-CH_2-CH_2-CN$$

and an extender.

3. A microbicidal agent according to claim 2, wherein said extender is selected from the group consisting of a liquid solvent and a solid excipient.

4. A microbicidal agent according to claim 2, wherein the 3-(3-iodopropargyloxy)-propionitrile is contained in an amount of 1 to 95% by weight.

5. A microbicidal agent according to claim 2, wherein the 3-(3-iodopropargyloxy)-propionitrile is contained in an amount of 10 to 75% by weight.

6. A method for the preservation of industrial materials comprising applying to said materials a microbicidally effective amount of a microbicidal agent, wherein said microbicidal agent being the agent of claim 2.

7. A method according to claim 6, wherein the concentration of the microbicidal agent is 0.001 to 5% by weight, based on the material to be preserved.

8. A method according to claim 6, wherein the concentration of the microbicidal agent is 0.05 to 1% by weight, based on the material to be preserved.

* * * * *